United States Patent [19]

Ferrara

[11] Patent Number: 4,809,694
[45] Date of Patent: Mar. 7, 1989

[54] BIOPSY GUIDE

[76] Inventor: Vincent L. Ferrara, 1501 Amity Rd., Rydal, Pa. 19046

[21] Appl. No.: 51,966

[22] Filed: May 19, 1987

[51] Int. Cl.$^4$ .............................................. A61B 17/00
[52] U.S. Cl. ................................................ 128/303 B
[58] Field of Search ................... 128/303 B, DIG. 26; 604/116, 177, 174, 180, 175, 178

[56] References Cited

U.S. PATENT DOCUMENTS 3,055,370  9/1962  McKinney et al. .................. 128/303
3,115,140 12/1963  Volkman ....................... 128/303 B X

*Primary Examiner*—Michael H. Thaler
*Attorney, Agent, or Firm*—Caesar, Rivise, Bernstein, Cohen & Pokotilow, Ltd.

[57] ABSTRACT

A guide for a medical instrument includes a cranial tap having a threaded end adapted to be secured into the skull of a patient, a spherical member having a passageway extending diametrically through it for receiving an instrument employed in a surgical procedure, and retaining structure attachable to the tap to immobilize the spherical member in a desired orientation within the tap, characterized in that the retaining structure includes first and second threaded members secured to the tap in different locations for engaging the spherical member in different locations to thereby retain the spherical member against movement within the tap. In a preferred embodiment of the invention the spherical member is deformable and one of the threaded members locally deforms the passageway extending diametrically through the spherical member to cause a surface of the passageway to frictionally engage an instrument extending through the passageway, and thereby prevent axial movement of the instrument relative to the spherical member.

3 Claims, 2 Drawing Sheets

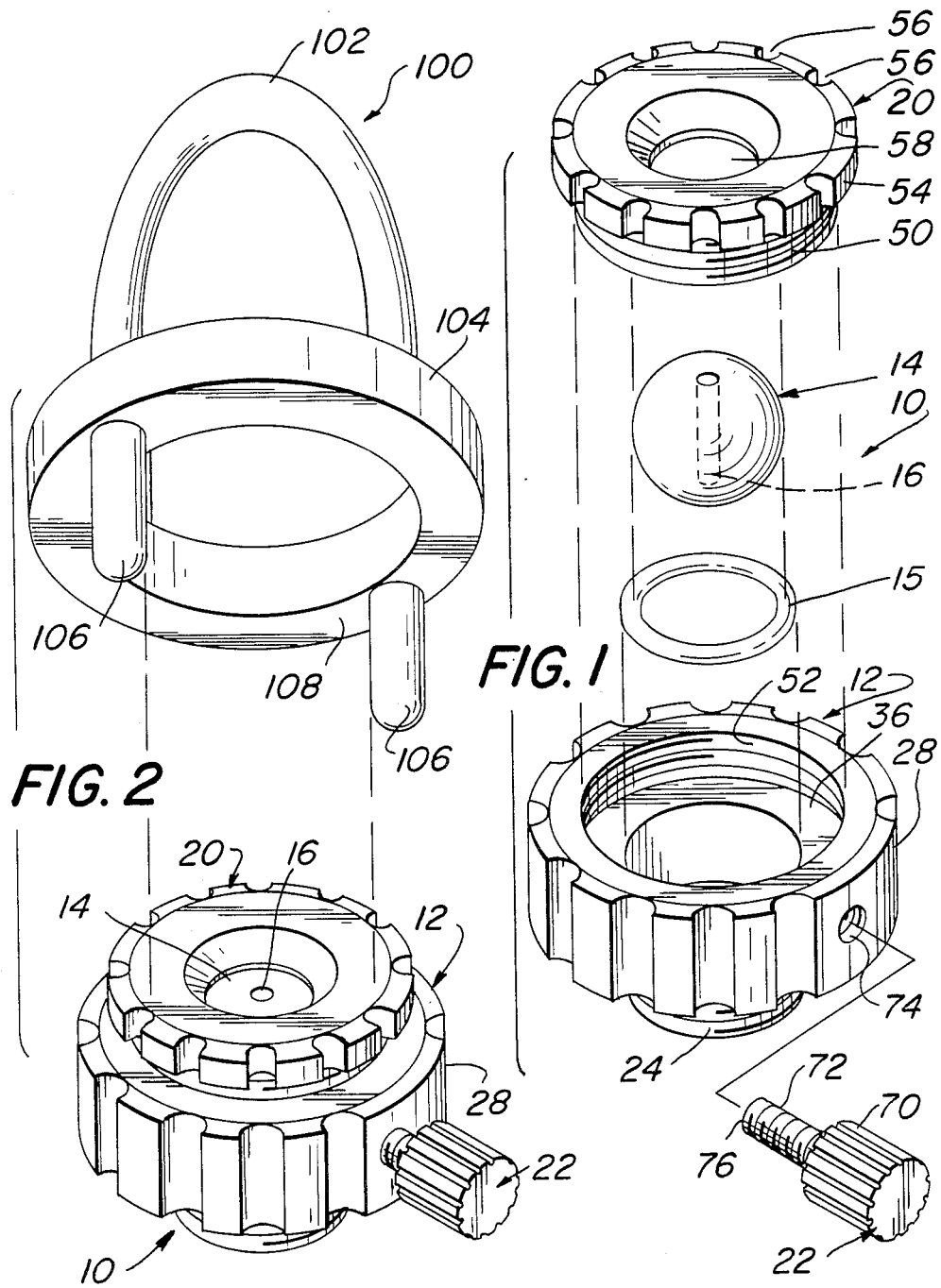

BIOPSY GUIDE

FIELD OF THE INVENTION

This invention relates generally to a guide for a medical instrument, and more specifically to a biopsy guide adapted to receive and properly position an instrument employed to remove tissue from within the brain of a patient.

BACKGROUND ART

A variety of guides employed to properly position a medical instrument within the skull of a patient are known in the prior art, as evidenced by the devices disclosed in the following U.S. Pat. Nos. 3,016,899—Stenvall, 3,017,887—Heyer, 3,021,842—Flood, 3,055,370—McKinney et al., 3,115,140—Volkman, 3,135,263—Connelley, Jr.

As is shown in the above identified McKinney et al. U.S. Pat. No. 3,055,370 a guide for a surgical instrument intended to be used in the treatment of the brain includes a cranial tap which is adapted to be threaded into the skull of a patient, a spherical member rotatable within the tap and adapted to receive the surgical instrument therein, and a locking cap threadedly received within the upper end of the tap to immobilize the spherical member. This arrangement positions the surgical instrument in a proper orientation for performing a desired medical procedure, such as rendering a portion of the brain ineffective by electrical stimulation to treat people afflicted with Parkinson's diease.

Although a guide of the type disclosed in the McKinney et al. patent has been employed with success, Applicant, who is a neurosurgeon, is of the opinion that a new and improved guide is desired which is simpler in design and yet reliable in use to properly position and retain a surgical instrument for use in performing a medical procedure, particularly within the brain.

OBJECTS OF THE INVENTION

It is a general object of this invention to provide a guide for a surgical instrument which is simple in construction and reliable in operation.

It is a more specific object of this invention to provide a guide for a surgical instrument which permits a great deal of latitude in positioning the instrument for performing a desired medical procedure.

It is a further object of this invention to provide a guide which is well suited for use in positioning a surgical instrument employed to take a biopsy of tissue in the brain.

It is a further object of this invention to provide a guide for a surgical instrument which is easily adjustable to properly orient a surgical instrument for performing a medical procedure, and also to positively lock the instrument within the guide so that it does not move relative to the guide.

SUMMARY OF THE INVENTION

The above and other objects of this invention are achieved with a guide for a medical instrument that is adapted to be secured to the skull of a patient, said guide including a cranial tap having a threaded end adapted to be secured into the skull, a spherical member rotatably received within a compartment of the tap and having a passageway extending diametrically therethrough for receiving the medical instrument to be guided, and retaining means for securing the spherical member against movement in a desired orientation, characteried in that said retaining means includes first and second threaded holding means for engaging said spherical member in different locations to thereby lock such spherical member against movement within the compartment of the cranial tap.

In a preferred embodiment of the invention the spherical member is made of a deformable material, such as a hard rubber, and one of the holding means engages an outer periphery of the spherical member for deforming the member, including at least a segment of the wall of the passageway through said spherical member, to thereby cause the wall of said passageway to frictionally engage the medical instrument, and thereby prevent axial movement of the instrument within the passageway.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 1 is an enlarged exploded isometric view of the guide in accordance with a preferred embodiment of the invention;

FIG. 2 is an enlarged exploded isometric view showing the guide of this invention and a wrench which is specially designed to screw the guide into the skull of a patient;

DESCRIPTION OF THE PREFERRED EMBODIMENTS OF THE INVENTION

Figure 3:
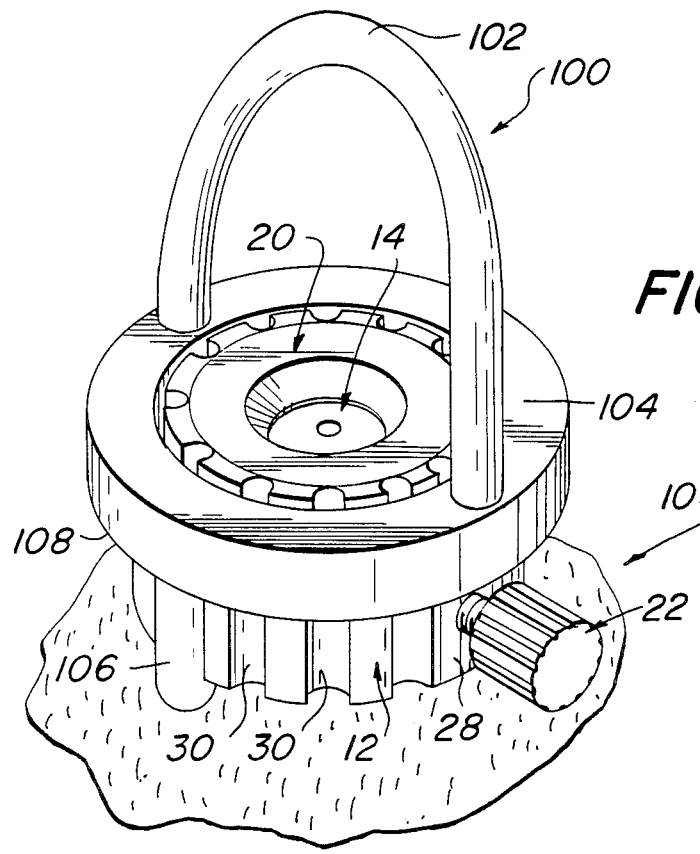
FIG. 3 is an enlarged isometric view similar to FIG. 1, but showing the wrench positioned on the guide, after the guide has been secured within the skull of a patient.

Referring now in greater detail to the various figures of the drawings wherein like reference characters refer to like parts, a guide for a medical instrument embodying the present invention is generally shown at 10 in FIG. 1. The device 10, which in the preferred embodiment is a biopsy guide for use in conjunction with an instrument intended to take a biopsy of brain tissue, basically comprises a cranial tap 12 to be screwed into the skull of a patient, an adjustable, spherical member 14 with a passageway 16 extending diametrically through it for receiving a medical instrument 18 (FIG. 4), said spherical member being retained within the cranial tap 12 on a rubber O-ring 5, and retaining means in the form of a threaded cap 20 and a threaded screw member 22 for positively locking the spherical member in a desired orientation within the tap 12, to properly position the instrument 18 therein. In a preferred embodiment of this invention the device is a biopsy guide and the instrumetn 18 is a biopsy needle employed in conjunction with a suction device for obtaining a biopsy of brain tissue.

Figure 4:
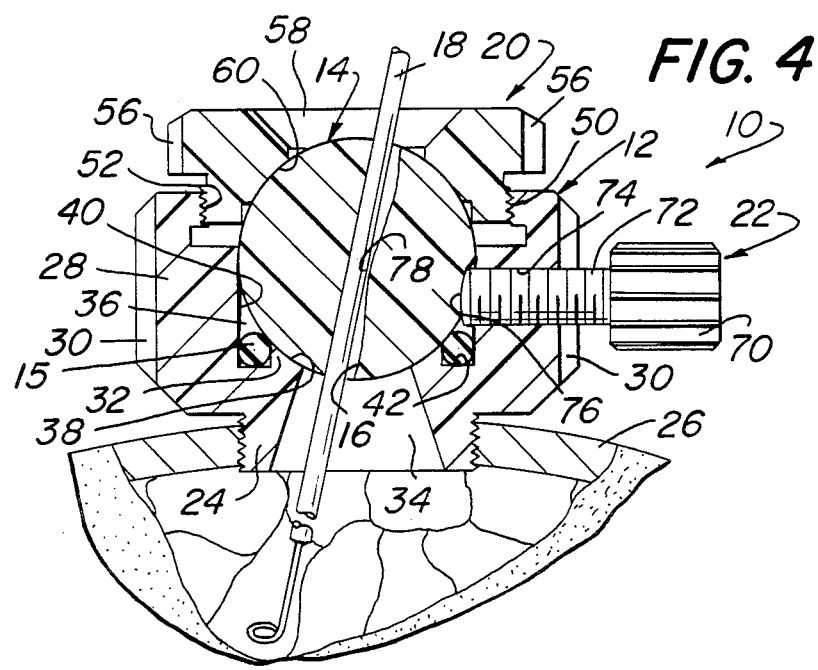
FIG. 4 is an enlarged fragmentary sectional view showing the guide of this invention secured to the skull of a patient, and a medical instrument retained within the guide in proper orientation to perform a surgical procedure.

Referring to FIGS. 1 and 4, the cranial tap 12 of this invention includes a lower threaded section 24 which is threaded into the skull 26 of a patient undergoing a neurosurgical procedure. The tap further includes an upper section 28 having a plurality of hemispherical grooves 30 spaced-apart about the circumference thereof. These hemispherical grooves 30 are adapted to cooperate with a wrench 100, in a manner which will be explained in detail hereinafter, to screw the tap 12 into the skull of the patient.

Referring specifically to FIG. 4, the tap 12 includes an inner annular support member 32 which surrounds, and partially defines an axial passage 34 that extends through the lower threaded section 24. This axial passage communicates with an upper compartment 36 in which the spherical member 14 is retained. It shoud be noted that an upper surface 38 of the annular support member 32 has a radius of curvature corresponding to that of the spherical member 14 to aid in supporting the spherical member.

Still referring to FIG. 4, the annular support member 32 cooperates with the radially spaced-apart annular surface 40 of the upper compartent 36 to define an annular groove 42 for receiving the rubber O-ring 15 therein. When the spherical member 14 is locked against movement within the guide 10, as illustrated in FIG. 4, it compresses against the O-ring 44 to provide an effective seal between the spherical member 14 and the tap 12, and also to provide an effective gripping action to aid in preventing movement of said spherical member.

Referring specifically to FIGS. 1 and 4, the cap 20, which constitutes part of the retaining means for the spherical member 14, includes a lower threaded section 50 that cooperates with a annular threaded section 52 on the upper section 28 of the tap 12. When the cap is screwed onto the tap it engages the spherical member 14 to assist in locking said spherical member in a desired orientation within the cranial tap. As can be seen best in FIG. 1 the cap includes an upper annular section 54 having knurls or grooves 56 in its outer side surface to provide a surface which can be easily manually gripped to permit the cap 20 to be threaded into the tap 12.

The cap 20 includes a passageway 58 extending axially through it to permit the instrument 18 to pass therethrough when the instrument is positioned within the passageway 16 of the spherical member, with the cap 20 threaded onto the tap 12. The passageway 58 includes an annular surface 60 (FIG. 4) intermediate the upper and lower surfaces thereof which has a curvature corresponding to that of the spherical member 14.

As can be seen best in FIG. 4, when the threaded cap 20 is secured to the cranial tap 12 the annular surface 60 of the cap engages the periphery of the spherical member 14, and presses the spherical member into engagement with the annular surface 38 provided on the inner annular support 32 of said cranial tap. In this position the O-ring 44 also is compressed against the periphery of the spherical member 14 to provide an effective seal between the spherical member and the cranial tap 12.

In accordance with this invention a second threaded retaining member, in the form of a threaded screw member 22, has an outer head 70 which is knurled to provide a surface which can be gripped easily by hand, and an inner threaded stem 72 for cooperating with threads on the peripheral surface defining a passageway 74 that extends laterally through the upper section 28 of the cranial tap 12. This passageway 74 extends completely through the upper section 28 to communicate with the upper compartment 36 in which the spherical member 14 is retained.

As can be seen best in FIG. 4 the threaded stem 72 has a distal end 76 which is adapted to engage the periphery of the spherical member 14, and thereby cooperate with the threaded cap 20 to firmly retain the spherical member in its desired orientation within the cranial tap 12.

Still referring to FIG. 4, in the most preferred embodiment of this invention the spherical member 14 preferably is constructed of a deformable material, such as a hard rubber member having a resiliency similar to that of the inner rubber section of a golf ball. In this embodiment of the invention the spherical member 14 is deformed by the localized force or pressure applied to the outer periphery thereof by the distal end 76 of the screw member 22. As is seen in FIG. 4 this local deformation is transmitted to a segment 78 of the peripheral wall defining the passageway 16, to thereby cause the wall of the passageway to grip the periphery of the instrument 18, and thereby prevent inadvertent and/or undesired axial movement of the instrument within the spherical member 14.

The ability to axially immobilize the medical instrument 18 within the spherical member 14 constitutes an important and unique feature in accordance with the most preferred embodiment of this invention. However, it should be understood that, in accordance with the broadest aspects of this invention, the spherical member 14 need not be made of a deformable material, in which case the threaded screw member 22 will function in cooperation with the threaded cap 20 to positively retain the spherical member 14 in a fixed orientation within the upper compartment 36 of the cranial tap 12, without deforming the walls of passageway 16.

Referring to FIGS. 1 and 3, a wrench 100 is illustrated for cooperating with the cranial tap 12, to assist in threading the tap into the skull of a patient. As can be seen in these figures the wrench 100 includes an upper U-shaped handle 102 which is connected to an annular intermediate member 104. Extending downwardly from the annular member 104 is a pair of diametrically opposed, cylindrical grippers 106 having a outer curvature generally conforming to the curvature of the grooves 30 that are spaced-apart about the periphery of the upper section 28 of the cranial tap 12. The manner in which the diametrically opposed grippers 106 cooperate with the grooves 30 can be seen best in FIG. 3. When the wrench 100 is completely seated on the device 10 the lower surface 108 of the annular rim 104 engages the upwardly facing surface of the cranial tap 12. In this position the handle 102 is turned in a clockwise direction to thread the tap 12 into the patients skull 26.

In accordance with the use of the device 10 a burr hole, on the order of 14 millimeters in diameter, initially is made in the patient's skull with a Hudson drill, or similar device. Thereafter a conventional burr hole enlarger is employed to increase the diameter of the opening to approximately 16 mm. Thereafter, the dura matter (i.e., the covering between the bone and the brain) is opened to permit access to the brain with a surgical instrument 18, such as a biopsy device.

At this point in the procedure the cranial tap 12 is threaded into the enlarged burr hole in the skull, the spherical member 14 is placed in the cranial tap 12 and the threaded cap 20 is threaded into the top of said tap. The patient then is taken to X-ray, where a CAT scan is employed to outline the lesion, tumor, clot or other abnormality requiring treatment. Under visual observation of the CAT scan the medical instrument 18 which is to be employed in the neurosurgical procedure is manipulated, or moved, within the passageway 16 of the spherical member 14 to properly position said instrument relative to the abnormality that is to be treated or acted upon. At this point both the threaded cap 20 and the threaded screw member 22 are tightened against the spherical member 14 to positively lock the spherical member 14 in its proper orientation. Moreover, in the most preferred embodiment of this invention, wherein the spherical member 14 is deformable, the tightening of the screw member 22 also deforms the wall of the passageway 16 in the spherical member 14 to firmly lock the instrument 18 within the spherical member, and thereby prevent undesired axial movement of the instrument into or out of the skull.

Without further elaboration, the forgoing will so fully illustrate my invention that others may, by applying current or future knowledge, adopt the same for use under various conditions of service.

What is claimed as the invention is:

1. A guide for a medical instrument adapted to be secured to the skull of a patient, said guide including a cranial tap having a lower threaded end for attachment within the skull of a patient; a spherical member having a passageway extending diametrically therethrough, said spherical member being rotatable within an upper compartment of said tap to position the passageway in a desired orientation, said tap having a passage extending through a lower surface thereof and communicating with the compartment in which the spherical member is retained, and retaining means for engaging the spherical member to secure said spherical member against movement within the compartment of said tap, said tap including an upper section having an opening at an upper end thereof for communicating with the upper compartment of the tap for permitting the spherical member to be inserted into said compartment, characterized in that said upper section of said tap includes a peripheral side wall and a threaded pasageway extending transversly through said side wall into communication with said upper compartment, said retaining means including first and second threaded members, said first threaded member being a cap means threaded into said opening at the upper end of said upper section of the cranial tap for engaging said spherical member and said second threaded member being a threaded screw member having a stem extending into said threaded passageway for engaging said spherical member, whereby said cap means and screw member engage said spherical member in different locations to positively lock said spherical member against rotational movement within the upper compartment of the cranial tap.

2. The guide of claim 1 wherein said spherical member is deformable under localized pressure applied thereto by a distal end of said stem to cause a region of a peripheral wall defining the passageway extending diametrically through said spherical member to deform into engagement with a medical instrument received within said passageway to thereby frictionally engage said instrument and prevent axial movement of said instrument within said passageway.

3. A guide for a medical instrument adapted to be secured to the skull of a patient, said guide including a cranial tap having a lower threaded end adapted to be secured to the skull of a patient, a spherical member having surface means defining a pasageway extending diametrically through said spherical member, said spherical member being rotatably adjustable within an upper compartment of said tap, said upper compartment including a lateral wall, said tap having a passage extending through a lower surface thereof and communicating with the upper compartment of said tap to permit an instrument received within the passageway of the spherical member to extend through the lower surface of the tap and into the tissue to be treated, and retaining means for holding the spherical member in a desired orientation within the compartment of the tap, characterized in that the spherical member is deformable and that the retaining member includes a member extending through the lateral wall of the tap for applying a localized pressure to the spherical member for deforming the surface means defining the pasageway extending diametrically through said spherical member to cause said surface means to frictionally engage a surface of the instrument extending through the passageway of said spherical member and thereby lock said instrument within the spherical member.

* * * * *